United States Patent [19]

Young

[11] Patent Number: 5,467,659
[45] Date of Patent: Nov. 21, 1995

[54] POWDER TESTER

[75] Inventor: David J. Young, Chorleywood, England

[73] Assignee: Eastman Kodak Company, Rochester, N.Y.

[21] Appl. No.: 313,523

[22] Filed: Sep. 26, 1994

Related U.S. Application Data

[63] Continuation of Ser. No. 956,540, Oct. 5, 1992, abandoned.

[30] Foreign Application Priority Data

Jan. 7, 1992 [GB] United Kingdom ............. 9200215

[51] Int. Cl.⁶ ............................................. G01N 33/00
[52] U.S. Cl. ............................................. 73/866
[58] Field of Search .................... 73/866, 9, 54.01, 73/54.03, 860

[56] References Cited

U.S. PATENT DOCUMENTS

| | | | |
|---|---|---|---|
| 3,221,560 | 12/1965 | Kosa et al. | 73/866 |
| 3,423,995 | 4/1966 | Scott et al. | 73/94 |
| 3,665,768 | 5/1972 | Hosokawa et al. | 73/866 |
| 3,940,997 | 3/1976 | Hudson . | |
| 4,062,228 | 12/1977 | Peak | 73/74 |
| 4,180,185 | 12/1979 | Yamamoto et al. | 222/57 |
| 4,181,023 | 1/1980 | Clamroth et al. | 73/432 |
| 4,243,059 | 1/1981 | Hammon et al. | 132/2 |
| 4,274,286 | 6/1981 | Gioia | 73/432 |
| 4,412,176 | 10/1983 | Kramer et al. | 324/204 |
| 4,607,532 | 8/1986 | Arthur et al. | 73/819 |
| 4,697,463 | 10/1987 | Spooner et al. | 73/866 |
| 4,766,761 | 8/1988 | Lee | 73/38 |
| 5,122,418 | 6/1992 | Nakane et al. | 424/401 |

FOREIGN PATENT DOCUMENTS

| | | |
|---|---|---|
| 560825 | 10/1932 | Germany . |
| 1773919 | 1/1973 | Germany . |
| 2658089 | 7/1977 | Germany . |
| 478192 | 7/1975 | U.S.S.R. . |
| 573739 | 9/1977 | U.S.S.R. . |
| 696379 | 11/1979 | U.S.S.R. . |
| 987468 | 1/1983 | U.S.S.R. . |
| 85/02678 | 6/1985 | WIPO . |

*Primary Examiner*—R. Raevis
*Attorney, Agent, or Firm*—Susan L. Parulski

[57] ABSTRACT

It is known that the properties of powders affect the ease or difficulty of handling in many industrial processes. In may cases, the only way to test the suitability of a particular powder for a given system is to pass a sample of that powder through the system. This involves using a large quantity of the material with the uncertainty that the properties of the material are in fact suitable for that system. Described herein is a test device which allows certain properties of a material in powder form to be determined without the need for large quantities of material. The device (10) comprises a frame (12, 14, 16, 18, 20) in which is mounted a curved test surface (26). An aperture (22) is provided in a top member (14) of the frame (12) to allow the material being tested to fall on to the test surface (26) to form a 'footprint'. The 'footprint' can then be measured to provide an indication of the properties of the material prior to it being introduced into a system in bulk.

11 Claims, 4 Drawing Sheets

POWDER TESTER

This is a continuation of application Ser. No. 956,540, filed 5 Oct. 1992, now abandoned.

FIELD OF THE INVENTION

This invention relates to testing devices and is more particularly concerned with testing devices for testing the physical properties of powders.

BACKGROUND OF THE INVENTION

Many industrial processes require the conveying, delivering, pouring and dispensing of bulk powders. A number of properties of the powder affect its ease or difficulty of handling and may include electrostatic charge, specific gravity, particle size, particle shape and particle size and shape distributions. Other factors which may affect the handling properties of the powder are the presence of residual amounts of synthetic precursors, particularly solvents, the hygroscopicity of the powder and its degree of aggregation.

While it may be theoretically possible to measure all of the parameters quantitatively and then predict how the powder would handle, this rarely happens. In practice, a powder is matched with an appropriate piece of handling equipment using the long and short term experience of the designers of that particular system.

It is quite likely that new powder types or batches could be put into an existing system and new or unexpected problems would occur. A powder can form 'bridges' and 'rat holes' in delivery hoppers, build up on sloping surfaces to form unacceptable mounds, stick to walls and billow in clouds into the working environment. All these problems are related in some way to the physical properties mentioned above.

As the properties of a powder are so difficult to quantify, it is probable that the only way to check if a new powder type or batch will handle satisfactorily in an existing system is to try it out in that system. This means that a significant quantity of the material, commonly several kilograms, is required with the doubt that the material may not be acceptable and therefore have to be rejected.

When it is intended to produce an improvement in the synthesis of preparation of a powder, it is commonly more convenient, and much less expensive, to produce initially just a few grams which can be tested for its handling properties.

GB-B-2 060 902 discloses an arrangement and method for measuring the flowability of powders. The arrangement comprises a cylinder into which the powder to be tested is loaded (called the fill), and a series of disks each having a different sized hole drilled therein, the disks being attached to the undersurface of the cylinder and through which the powder is caused to pass. The arrangement operates on the principle that a free flowing powder slowly flows even through small holes until an inverted cone is formed in the whole thickness of the fill while a powder which flocculates into a mass falls as a lump leaving a cylindrical cavity in the fill. A positive result is obtained if the flow of powder begins within 60s and continues until a cavity of conical or cylindrical shape is formed in the whole thickness of the fill. If the test is positive, a smaller-sized hole will be used. Similarly, if the test is negative, a larger-sized hole is used.

The method described in GB-B-2 060 902 is time dependent, each run lasting at least 60s, and is repetitive regardless of whether a positive result is obtained during the first run. This method still needs a significant amount of powder and may still not predict how the powder falls past or builds up on a given surface.

SUMMARY OF THE INVENTION

It is therefore an object of the present invention to provide a simpler arrangement in which the properties of small quantities of powder may be tested very simply and non-destructively, in order to predict how the powder will handle in large quantities throughout a piece of equipment.

In accordance with one aspect of the present invention, there is provided a testing device for testing the handling properties of a sample of a powder comprising:

a frame comprising at least two members positioned to be substantially orthogonal to one another;

a test surface mounted on the frame; and aperture defining means associated with the frame for allowing a sample of powder to be introduced into the device under predetermined conditions and to be incident on the test surface;

characterized in that the test surface comprises a substantially curved surface.

BRIEF DESCRIPTION OF THE DRAWINGS

For a better understanding of the present invention, reference will now be made, by way of example only, to the accompanying drawings in which.

DETAILED DESCRIPTION OF THE INVENTION

Figure 1:
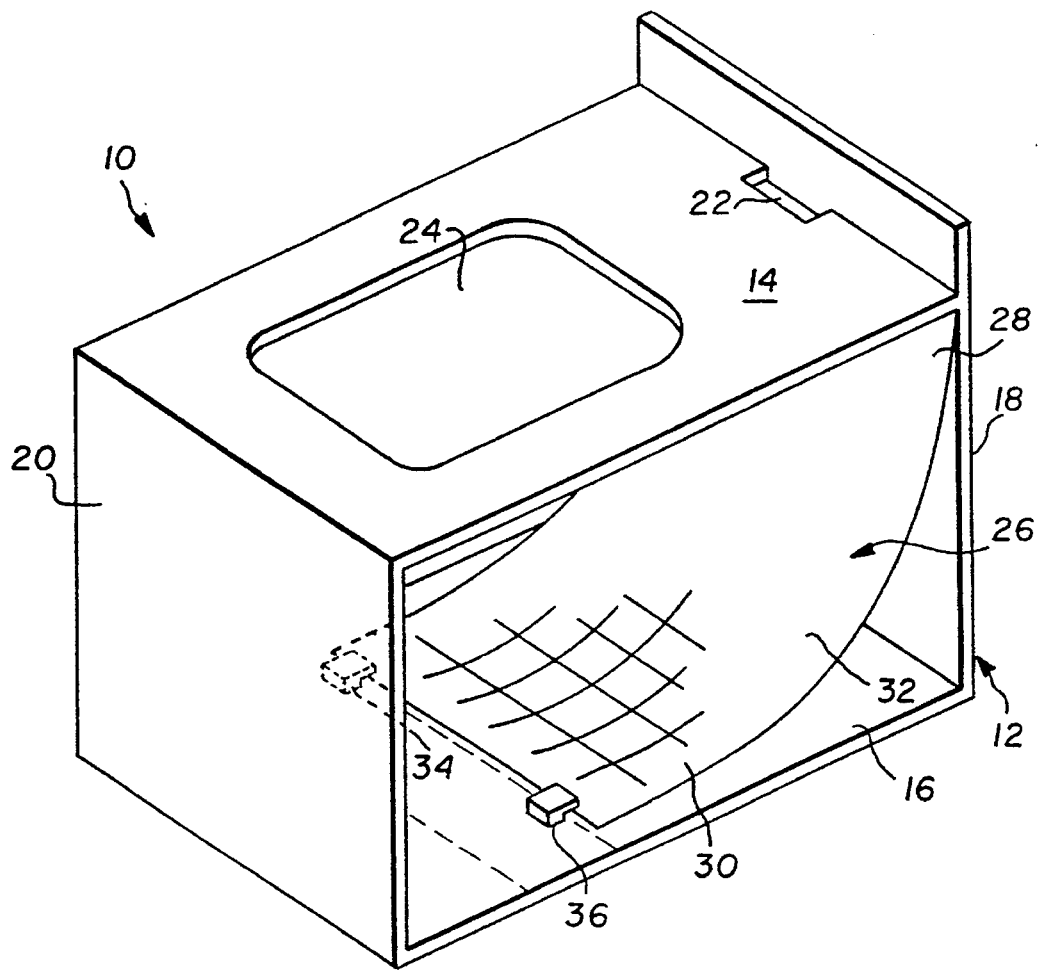
FIG. 1 is a perspective view of a testing device constructed in accordance with the present invention.

In FIG. 1, a device 10 in accordance with the present invention is illustrated. The device comprises a frame 12 in the form of an open-sided cuboid which includes a horizontal top member 14, a horizontal bottom member 16, and a pair of opposed vertical end members 18, 20. An aperture 22 is formed in the top member 14 adjacent end member 18 and through which the material to be tested is introduced into the device 10. A viewing aperture 24 is also provided in the top member 14.

A test surface 26 is positioned within the frame 12 as shown so that first portion 28 lies against the vertical end member 18, second portion 30 lies along the horizontal bottom member 16 and a third portion 32 between portions 28, 30 forming a curved surface connecting them. Moreover, as shown in FIG. 1, the first portion 28 of test surface 26 is substantially vertical at a location substantially adjacent aperture 22 and second portion 30 is substantially horizontal at a location remote from the aperture 22. A pair of pegs 34, 36 are attached to the bottom member 16 to provide a stop for the free end of portion 30, and to retain the test surface 26 in the correct position.

The test surface 26 may be made of any suitable flexible material, for example, card, polished aluminium plate, brushed aluminium plate, polyethylene teraphthalate, and gelatin-coated polyethylene teraphthalate.

Figure 2:
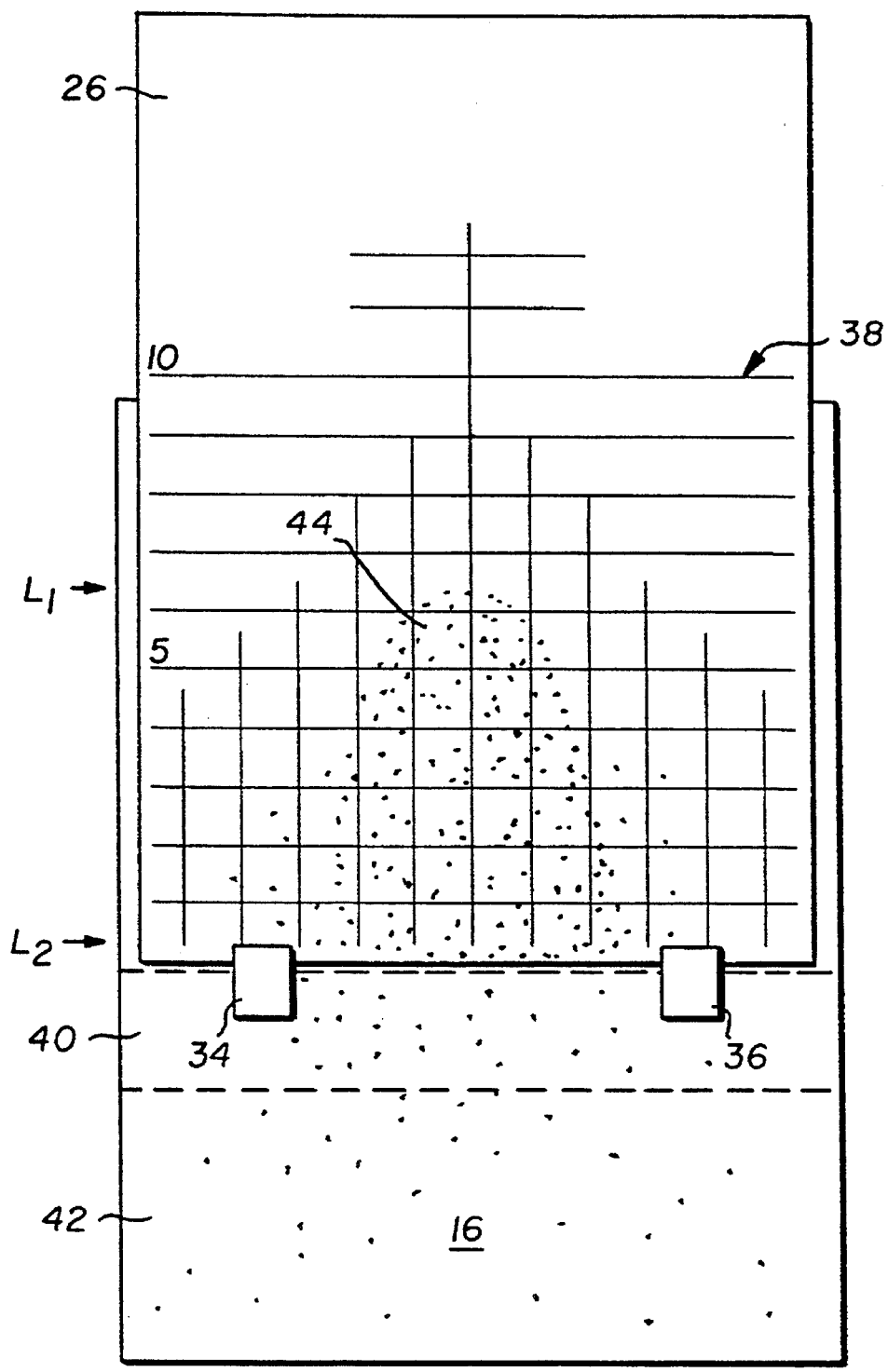
FIG. 2 is a plan view of a test surface used in the device shown in FIG. 1.
Figure 3:
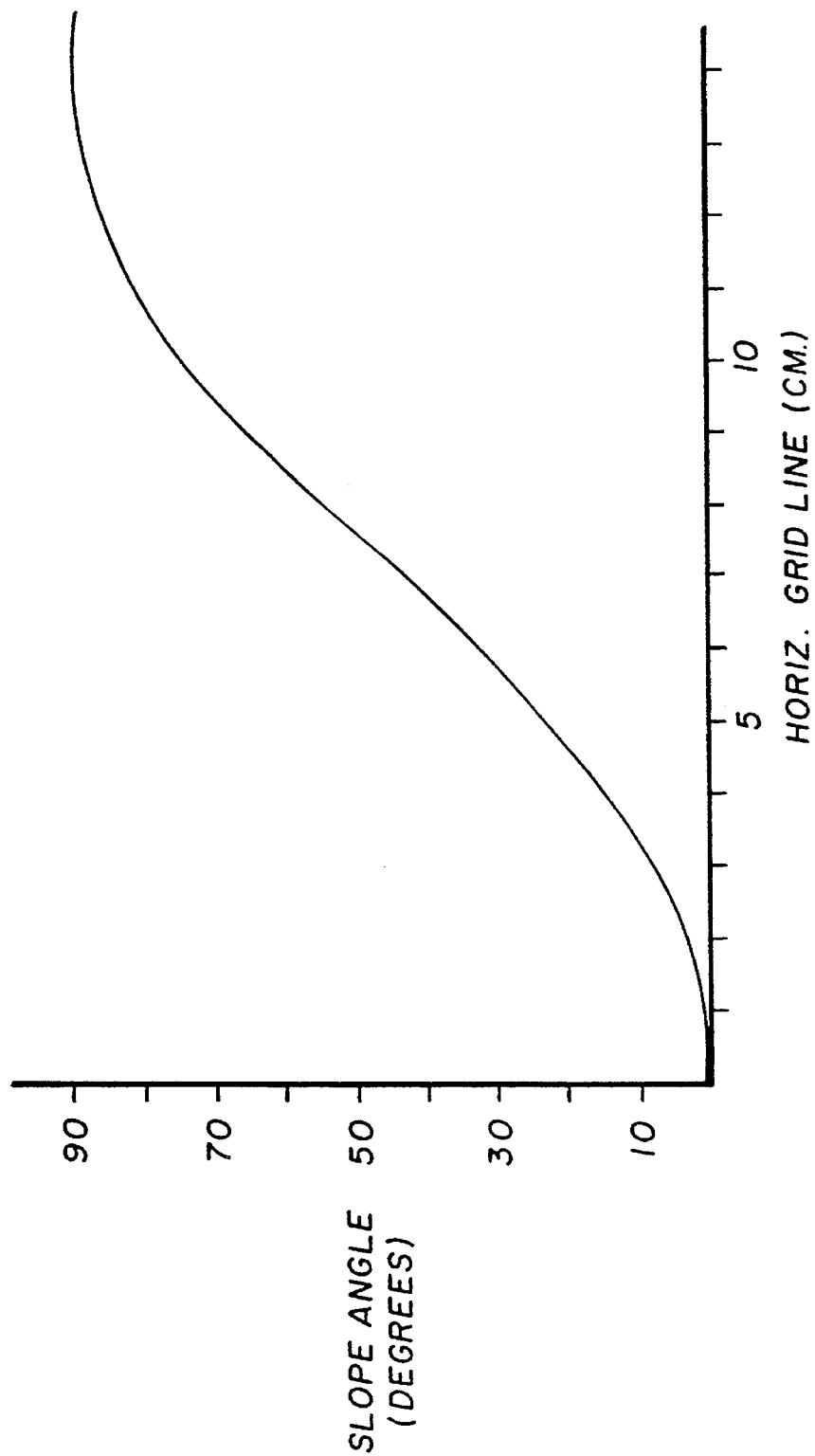
FIG. 3 is a graph showing the calibration of the test surface in terms of grid lines and slope angle.
Figure 4:
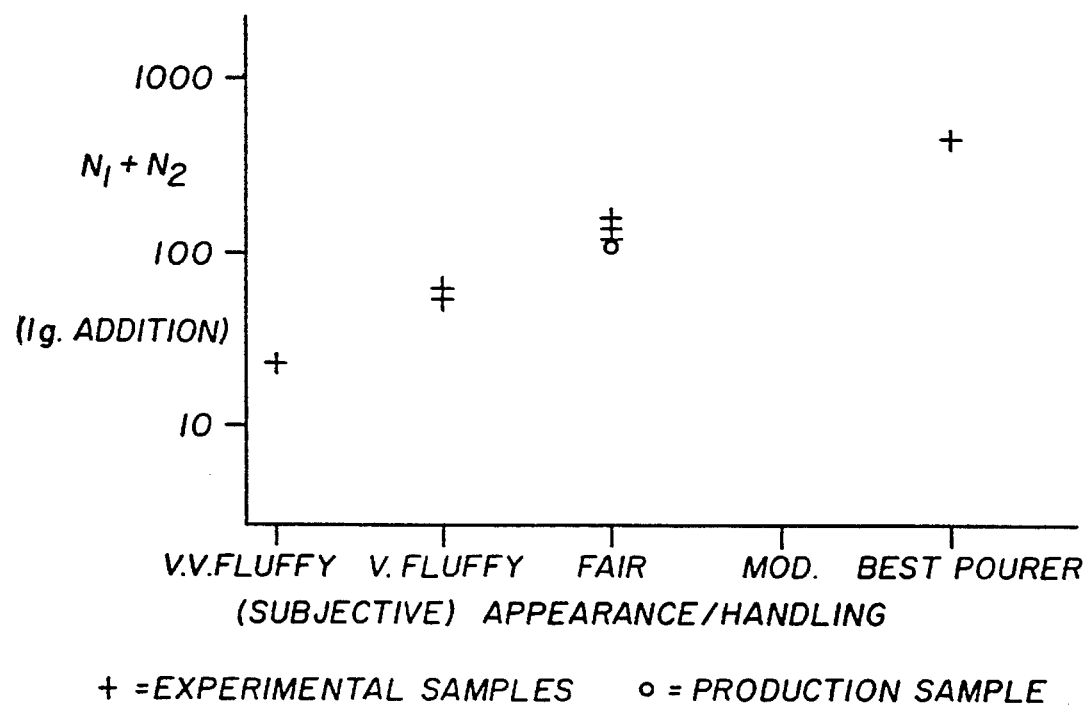
FIG. 4 is a graph illustrating a relationship between the number of aggregated particles falling beyond the test surface and subjective appearance/handling.
Figure 5:
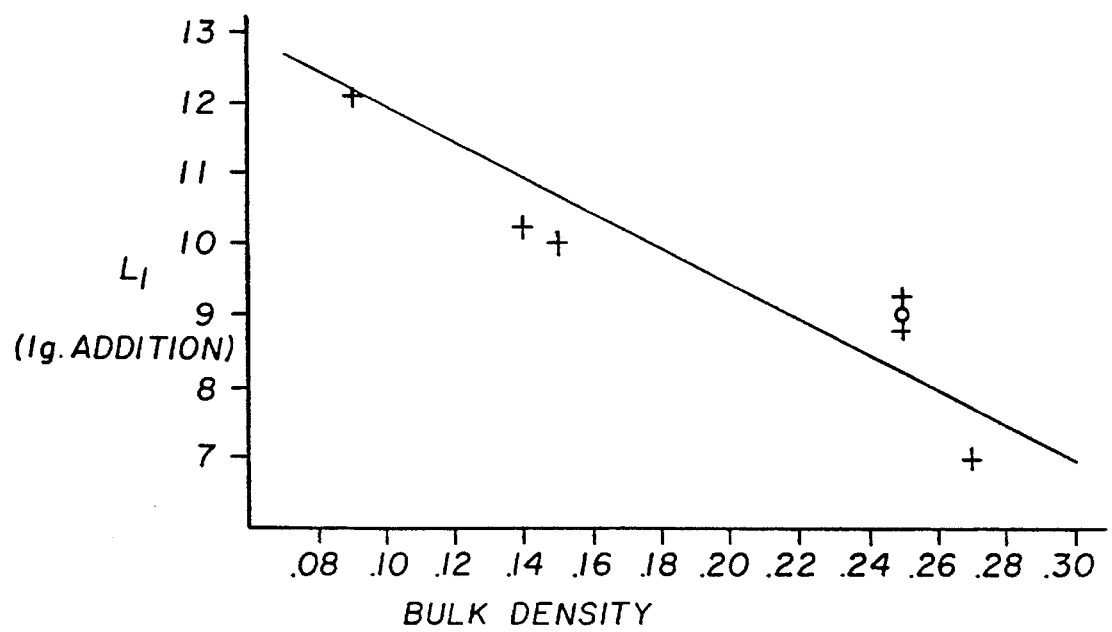
FIG. 5 is a graph illustrating a relationship between the highest distance of continuous powder up the test surface and the bulk density of the material being tested.

In FIG. 2, the test surface 26 is shown in plan view. The surface 26 is shown in its position relative to the bottom member 16 and pegs 34, 36. A grid 38 is marked on to the surface 26 so that quantitative information relating to the powder(s) being tested can be derived. The grid shown in this case comprises a series of lines 1 cm apart and which run in mutually perpendicular directions extending along and across the test surface 26 to form a series of squares having sides of 1 cm. Two further test areas 40, 42 are preferably defined by the bottom member 16 as shown.

In operation, powder to be tested is introduced into the device 10 through the aperture 22. This provides a reference point from which the powder can be introduced into the device, the point being at a fixed height and position above the test surface 26. The powder then falls on to the test surface 26 and forms a 'footprint' 44 on the grid 38.

One possible 'footprint' is shown in FIG. 2. From the grid 38, the following information can be determined (all distances being given in cm):

1) $L_1$ is the highest distance of continuous powder up the test surface;
2) $L_2$ is the lowest distance of continuous powder down the test surface;
3) $W_1$ is the maximum width of continuous powder;
4) $W_2$ is the widest spread of powder particles on the test surface (neglecting one or two outlying particles);
5) $N_1$ is the number of (usually) aggregated particles in area 40; and
6) $N_2$ is the number of (usually) aggregated particles in area 42.

It has been found by experiment that the size and shape of the resulting 'footprint' of powder is very reproducible. Using a powder comprising α-[4-( 4-benzyloxyphenylsulphonyl)-phenoxy]-α-(pivalyl)-2-chloro-5-[γ(2,4-ditertamylphenoxy)butyramido]-acetanilide and a test surface made of card, the results shown in Table 1 were obtained.

TABLE 1

| RUN | POUR RATE | $L_1$ | $L_2$ | $W_1$ | $N_1 + N_2$ |
| --- | --- | --- | --- | --- | --- |
| 1 | medium | 8.1 | 3.3 | 3.0 | 2 |
| 2 | fast | 8.2 | 3.3 | 2.8 | 1 |
| 3 | slow | 8.0 | 2.9 | 3.1 | 0 |
| 4 | medium | 8.0 | 3.0 | 3.3 | 1 |
| 5 | medium | 8.2 | 3.1 | 2.9 | 2 |

The mean and standard deviations for $L_1$, $L_2$ and $W_1$ are 8.1 & 0.10, 3.1 & 0.18, and 3.0 & 0.19 respectively.

It is also clear that the rate of pouring of the powder through the aperture has little, if any, effect on the dimensions of the 'footprint'.

It was also found by experiment that the properties of the test surface only has a modest effect on the shape of the 'footprint'. Table 2 illustrates the results for three different powders on the four different test surfaces, the same test-surfaces being used for each of the three powders. Other powders and other surfaces may produce different results.

The three powders are as follows:

Powder A: 1-(2,4,6-trichlorophenyl)-3-{5-[α-( 3-tertbutyl-4-hydroxyphenoxy)tetradecanamido]-2-chloroanilino}-5-pyrazolone Powder B: α-[4-(4-benzyloxyphenylsulphonyl)phenoxy] -α-(pivalyl)- 2-chloro-5-[γ(2,4-ditertamylphenoxy)butyramido]-acetanilide Powder C: 2-[α-(2,4-ditertamylphenoxy)butyramido]-4,6-dichloro-5-ethyl-phenol The four test surfaces are as follows:

Surface W: gelatin-coated polyethylene terephthalate

Surface X: polished aluminium

Surface Y: brushed aluminium

Surface Z: card

TABLE 2

| | BULK DENSITY (g/cm³) | SURFACE | $L_1$ | $W_1$ | $N_1$ | $N_2$ |
| --- | --- | --- | --- | --- | --- | --- |
| A | 0.25 | W | 9.6 | 3.3 | 50 | 50 |
| A | 0.25 | X | 9.1 | -4 | 90 | 65 |
| A | 0.25 | Y | 8.9 | 3.5 | 100 | 60 |
| A | 0.25 | Z | 9.1 | 3.2 | 70 | 50 |
| B | 0.59 | W | 8.4 | 3.0 | TOTAL 0 | |
| B | 0.59 | X | 7.9 | 3.5 | TOTAL 1 | |
| B | 0.59 | Y | 8.3 | 2.8 | TOTAL 3 | |
| B | 0.59 | Z | 8.1 | 3.0 | TOTAL 2 | |
| C | 0.5 | W | 8.3 | 3.3 | 7 | 2 |
| C | 0.5 | X | 8.3 | 3.0 | 6 | 0 |
| C | 0.5 | Y | 8.5 | 3.3 | 7 | 3 |
| C | 0.5 | Z | 8.8 | 3.2 | 9 | 2 |

Although it was relatively easy to measure the 'footprint' of many samples of powder, it was difficult to relate these measurement to quantitative properties of the bulk powder. Indeed it is the purpose of this device to generate quantitative measures of hitherto subjective or qualitative properties of powders.

However, it the observed handling properties of the powder which are of most interest, for example, the 'slumping', 'stickiness', and 'fluffiness', rather than the physical or chemical properties defining, for example, the bulk density, surface charge, residual solvent, particle size and shape. A number of qualitative relationships may be suggested as follows:

| PROPERTY | POSSIBLE MEASURE |
| --- | --- |
| adhesion to a sloping surface | $L_1$ |
| spread of particle size | $L_2$ |
| percentage of aggregate particles | $N_2$ |
| size distribution of aggregates | $N_1:N_2$ |
| lightness/fluffiness | $W_2, N_1, N_2$ |
| interparticle repulsion | $W_1, W_2$ |

It is not suggested that the above parameters are unique and the only measures of the indicated properties, and more quantitative and qualitative relationships may emerge from experiments using a wider range of compounds. So far, it has been found that for each powder tested a different set of parameters (L, W, N) describe the powder footprint as shown in Table 2.

The device of the present invention is small, simple to use and inexpensive. It requires only a small amount of material for the test and enables a quantitative, or semi-quantitative series of measurements to be applied to any given powder sample. Furthermore, it is light and compact, and as no power supply is required, the device can be operated anywhere.

It was found that for one particular powder, the application of an ultrasonic probe to the test surface for a few seconds caused the powder to slump rapidly to the bottom of the test surface. This suggests that the application of ultrasonic energy to a feed hopper containing this powder would significantly improve its flow out of the hopper. This indicates that the application of an ultrasonic transducer (possibly one having a variable frequency) to the test surface might enhance the utility of the device. (Although this would introduce the need for an electrical power supply.)

Although the device has been applied to powders A, B and C listed above, other powders could equally well be tested in this manner.

The size of the device discussed above is approximately 17 cm×13 cm×12 cm and is already of a size enabling it to be portable. The device could be folded to be substantially flat or could be dismantled to lie substantially flat thereby making it more portable.

Test surfaces could be made of any suitable material, although only three materials and five surfaces have been described herein. Materials such as plastics, and metals other than aluminium, could also be used. Furthermore, the surface properties of the materials used could be rough, polished, electrostatically charged, magnetic, earthed, hydrophobic or hydrophillic or a combination of these, or ultrasonically agitated as mentioned above.

The invention has been described in detail with particular reference to a preferred embodiment thereof, but it will be understood that variations and modifications can be effected within the scope of the invention.

I claim:

1. An apparatus for testing the handling properties of a sample of powder, comprising:
    a frame;
    a stationary test member mounted to the frame, the test member having a substantially curved test surface with an upper portion;
    a grid marked on the test surface for deriving quantitative information about a sample of powder; and
    means for introducing the sample of powder onto the upper portion of the test surface, such that the sample of powder moves downward along the test surface and comes to rest on the grid, thereby allowing a quantitative derivation of information on the sample of powder.

2. An apparatus according to claim 1 wherein said frame includes a top member, a bottom member, and opposing end members structurally interconnecting said top and bottom members.

3. An apparatus according to claim 2, wherein the frame is substantially rectangular in cross-section and wherein the test surface is mounted between one of said end members and the bottom member.

4. An apparatus according to claim 2, wherein the bottom member includes stop means for defining the location of one end of the test surface.

5. An apparatus according to claim 4, wherein the means for introducing is formed in the top member remote from the stop means.

6. An apparatus according to claim 1 wherein said test member is flexible.

7. An apparatus according to claim 1, wherein the test surface includes a first portion which is substantially vertical at a location substantially adjacent the means for introducing.

8. An apparatus according to claim 1, wherein the test surface includes a second portion which is substantially horizontal at a location remote from the means for introducing.

9. An apparatus according to claim 1, wherein the grid is rectilinear.

10. A device according to claim 1, wherein the device is collapsible for storage or carriage.

11. A method for testing the handling properties of a sample of powder, comprising the steps of:
    positioning a test member stationarily in a frame such that the test member has a substantially curved test surface with an upper portion and a grid marked thereon;
    introducing a sample of powder onto the upper portion of the test surface, and allowing the sample of powder to move downward along the test surface and come to rest on the grid; and
    measuring the sample of powder on the grid to derive quantitative information.

* * * * *